(12) United States Patent
Bosio

(10) Patent No.: US 7,378,279 B2
(45) Date of Patent: May 27, 2008

(54) EXAMINATION DEVICE AND METHOD FOR EXAMINATION OF CHEMICAL AND/OR BIOLOGICAL SAMPLES

(75) Inventor: Andreas Bosio, Cologne (DE)

(73) Assignee: Memorec Biotec GmbH, Cologne (DE)

( * ) Notice: Subject to any disclaimer, the term of this patent is extended or adjusted under 35 U.S.C. 154(b) by 804 days.

(21) Appl. No.: 10/472,132

(22) PCT Filed: Mar. 15, 2002

(86) PCT No.: PCT/EP02/02900

§ 371 (c)(1),
(2), (4) Date: Mar. 8, 2004

(87) PCT Pub. No.: WO02/075280

PCT Pub. Date: Sep. 26, 2002

(65) Prior Publication Data

US 2004/0147041 A1    Jul. 29, 2004

(30) Foreign Application Priority Data

Mar. 16, 2001    (DE)    ................. 101 12 683

(51) Int. Cl.
 *G01N 1/31* (2006.01)
 *G01N 1/00* (2006.01)
 *C12Q 1/68* (2006.01)
(52) U.S. Cl. .............. 436/47; 436/174; 422/68.1; 435/6; 435/287.2
(58) Field of Classification Search ............ 422/102, 422/100, 99, 104, 68.1; 436/174, 180; 435/283.1, 435/288.3, 6, 287.2; 350/535, 536
See application file for complete search history.

(56) References Cited

U.S. PATENT DOCUMENTS

| 4,847,208 A | 7/1989 | Bogen |
| 6,129,828 A | 10/2000 | Sheldon, III et al. ........ 204/518 |
| 6,623,701 B1 * | 9/2003 | Eichele et al. .............. 436/174 |

FOREIGN PATENT DOCUMENTS

| EP | 1 081 233 | 7/2000 |
| JP | 61029734 | 2/1986 |

OTHER PUBLICATIONS

PCT International Preliminary Examination Report for corresponding International Application No. PCT/EP2002/00290 (English Translation).

* cited by examiner

*Primary Examiner*—Walter D. Griffin
*Assistant Examiner*—Christine T Mui
(74) *Attorney, Agent, or Firm*—Ohlandt, Greeley, Ruggiero & Perle L.L.P.

(57) ABSTRACT

An analyzing device for analyzing chemical and/or biological samples comprises a plurality of base parts, e. g. object holders, in a receiving device. The base parts are closed by a lid which is configured such that each base part and the lid form a test chamber for receiving the sample. Further, a conveying means for moving the sample in the test chamber is provided. The pumps of the conveying means are connected via channels with the test chamber and are controlled such that a portion of the sample liquid is alternately drawn off the test chamber and supplied back thereto by the pumps.

16 Claims, 4 Drawing Sheets

EXAMINATION DEVICE AND METHOD FOR EXAMINATION OF CHEMICAL AND/OR BIOLOGICAL SAMPLES

FIELD OF THE INVENTION

The invention relates to an analyzing device and a method for analyzing chemical and/or biological samples.

DISCUSSION OF THE BACKGROUND ART

With such analyzing devices, tissue samples, for example, are analyzed by means of a hybridization process. In this connection, DNA pieces, for example, i.e., gene fragments, are applied upon the surface of an object holder. Applying the DNA pieces is effected by dripping by means of a robot. Thus, the position of the individual DNA pieces on the object holder is known. The DNA pieces connect with the surface of the object holder and adhere thereto so that their positions do not change in the subsequent analyzing process.

From a tumor to be examined, for example, RNA is taken in the next step. By means of enzymes, the RNA is transformed into DNA and subsequently marked with suitable markers, particularly fluorescent color markers.

Additionally, a comparative sample with healthy tissue is produced. The healthy DNA is also marked with a suitable marker. Preferably, the marker is a fluorescent marker of another color so that the healthy tissue is marked with a greenly fluorescent marker and the tissue to be analyzed taken from the tumor, for example, with a red color marker.

Subsequently, both samples are applied onto the entire object holder. The DNA strands included in the two samples firmly connect to the counterparts, i.e., the DNA pieces present on the surface of the object holder. Connecting the DNA included in the samples with the DNA pieces adhering to the object holder is effected in a hybridization process. Subsequently, the object holder is washed so that only firmly adhering DNA pieces and chained-up DNA from the two samples is present on the object holder.

After the object holder has been dried, it is put through to a detecting process. Therein, the individual positions of the object holder to which DNA pieces adhere are analyzed by a suitable microscope. In doing so, the individual DNA pieces are stimulated by laser light, for example, so that the fluorescent markers fluoresce in the corresponding color. If a certain position to which a DNA piece adheres appears as a red spot, for example, it can be concluded therefrom that this gene was active in the tumor tissue but not in the healthy tissue. If a spot fluoresces greenly, it can be concluded therefrom that this gene was only active in the healthy tissue. In the case of yellow fluorescence occurring, the corresponding gene was active in both tissues. By the above method, it can be diagnosed which genes are active in a tumor, for example. Therefrom, conclusions as to the kind of tissue change and the like can be drawn.

In order to realize an as good connection of the two samples with the DNA pieces on the object holders as possible, it is known to close the object holder by a lid, for example, so that a test chamber is formed between the object holder and the lid. Then, the test chamber is vibrated by a vibration means to effect a movement of the two samples. By this movement, it is easier for the corresponding sample components to find the suitable counterparts with which they then connect. Providing a vibration means has the disadvantage that stationary waves are produced and thus, only a limited movement of the sample occurs.

The problems described in the example above also exist in other analyses of chemical and/or biological samples in which one sample, for example, firmly adheres to a base part such at the object holder and another sample is to react on it.

SUMMARY OF THE INVENTION

It is an object of the invention to increase the probability of occurrence of reactions in samples.

The analyzing device according to the invention comprises a base part and a head part or lid. The base part and the head part form a test chamber. The base part may be a flat object holder, for example, made of thin glass. Likewise, the object holder or another sample holder may be placed upon the base part so that the sample holder is arranged within the test chamber. Further, the device according to the invention comprises a moving means for moving the sample in the test chamber. According to the invention, the analyzing device comprises a conveying means as a moving means. By means of the conveying means, at least a part of the sample is sucked off the test chamber and subsequently supplied to the test chamber again. Conveying of a part of the sample can be effected by moving the sample to and fro in that a part of the sample is sucked off and supplied back in opposite direction. For this purpose, at least one channel is preferably connected with the test chamber, which channel is preferably connected with a pump or another conveying means for moving the sample to and fro. Another possibility for moving the sample in the test chamber is to circulate the sample. In this case at least a part of the samples is preferably sucked off via a discharge channel and preferably supplied back to the test chamber via a supply channel. In this case the sample is supplied in the same direction.

By providing, according to the invention, a conveying means as a moving means for the sample, the occurrence of stationary waves is avoided. By sucking off and supplying a part of the sample, it is ensured that the entire sample quantity present in the test chamber is moved. This is ensured in the case of both moving at least a part of the sample to and fro and circulating at least a part of the sample.

Depending on the size of the test chamber, this can be ensured in a first preferred embodiment of the invention by sucking off a sufficient amount of the sample and subsequently supplying it to the test chamber again. Therefore, a receiving chamber for receiving and subsequently delivering a part of the sample is preferably provided between the conveying means which, for example, is a pump, and the test chamber. By dimensioning the receiving chamber correspondingly, a large part of the sample located in the test chamber can be sucked off and subsequently supplied to the test chamber again, for example. Instead of a separate receiving chamber, a channel located between the conveying means and the test chamber can be dimensioned correspondingly and serve as receiving chamber.

In a particularly preferred embodiment, at least two receiving chambers are provided. They are connected with one or two conveying means such that a part of the sample is alternately received and delivered by the test chambers. While a sample is delivered from the one receiving chamber, for example, a sample can simultaneously be received in the other test chamber. Thereby, a uniform movement of the sample in the test chamber is realized. There may also be an interval between the delivery of the sample from the one receiving chamber and the reception of the sample in the other receiving chamber. Further, the two processes may overlap.

For improving the movement of the sample in the test chamber, several channels, preferably in the head part or the lid, can be arranged through which the sample is extracted from the test chamber at different sites and, supplied thereto again. The extraction site may possibly also differ from the supply site so that the sample is delivered "in a circle".

In a second preferred embodiment of the invention, the sample in the test chamber is circulated. For this purpose, the test chamber is connected with a supply channel and a discharge channel. Both the supply channel and the discharge channel are connected with the conveying means, e.g. the pump. Preferably, a valve is connected with the discharge channel, which valve is also connected with a drain. The sample can thus be drawn off or sucked off the test chamber with the aid of the conveying means and then, depending on the position of the valve, be supplied partly or completely in the direction of the drain. The drain is preferably connected with a collection tank in which a used sample liquid is collected and subsequently disposed of. By correspondingly switching the valve it is possible always to draw off a part of the circulated sample in predetermined intervals. To be able to exchange the sample partly or completely, the conveying means is preferably connected with a medium reservoir. Thus the valve can be opened such that always a part of the circulated sample is discharged, and the sample amount discharged from the medium reservoir is topped up. This results in a continuous exchange of a part of the sample. Of course, it is also possible to completely close the valve so that the sample is circulated, or to completely open the valve so that the entire sample amount in the test chamber is discharged.

Preferably, the test chamber is formed by a corresponding configuration of the head part or the lid, such as a circumferential frame-shaped projection provided at the lid. This has the advantage that a conventional object holder, a flat glass plate, for example, can be used as a base part. The frame-shaped projection provided at the lid preferably comprises a circumferential seal so that the test chamber is sealed to the outside and no sample liquid can escape from between the lid and the base part.

In addition to or instead of providing a projection at the head part or the lid it is also possible to use a frame-shaped intermediate part. The use of a frame-shaped intermediate part offers the advantage that the latter can be removed for cleaning purposes. Further, it is possible to define the test chamber volume via the thickness of the intermediate part. By exchanging the intermediate part, the volume is thus easily variable.

In a particularly preferred embodiment, a receiving device for several object holders is provided. The receiving device comprises a bottom part and centering elements connected with the bottom part. Through the centering elements, several receiving areas for receiving one object holder, respectively, are configured. Thus, one object holder per receiving area can be laid onto the bottom part. Then, the object holder serves as base part and forms a test chamber together with a lid. To this end, a separate lid per receiving area can be provided. It is also possible to provide a common lid formed correspondingly for several receiving areas.

Thus, one object holder, to which DNA pieces already adhere at predetermined positions, for example, can be laid in the receiving areas of the receiving device, respectively. Then, the receiving device carrying several object supports can be easily handled by means of robot grip arms or the like, for example. Since the receiving device can be easily gripped at the centering elements or at the bottom part, for example, handling the object holders is easily possible. By the device according to the invention, it is particularly ensured that object holders of thin glass are not damaged during handling. Touching the samples already located on the object holders is avoided as well.

Preferably, the centering elements are configured like integral frame parts. Thus, each object holder is surrounded by a frame. This has the advantage that the object holder is disposed in the receiving area in a protected manner. Preferably, the frame part has a height higher than the thickness of the object holder so that the object holder is received completely within the frame part. Thereby, damaging the object holder upon handling the receiving device as well as touching the surface of the object holder are avoided. Preferably, several receiving areas are formed by a single frame part. In this case, each receiving area is completely surrounded by a frame. A wall of the frame part provided between two neighboring object holders thus serves as portion of the frame of two receiving areas.

Each of the above-described frame parts may surround a receiving area, preferably completely as a circumferential centering frame. But they may also be individual frame parts not surrounding the receiving areas but only serving, for example, to receive corners of the object holder to center the latter in the receiving device. In this case, inserting the object holders into the receiving device is possibly made easier. For making the insertion of the object holders into the receiving device easier, the centering elements may further be chamfered. The chamfer is configured such that the receiving area in which one object holder is respectively received is enlarged upwards to make the insertion of an object holder easier.

In a particularly preferred embodiment, the bottom part comprises a flexible material at least in the receiving areas. Particularly, the entire bottom part consists of a continuous flexible material. The object holders rest on this flexible material. The use of flexible material offers the advantage that, if the object holders are touched by pipettes or the like, a certain degree of resilience of the object holders is ensured. This reduces the risk of damage to the object holders during the analyzing process. Further, it is possible to align the object holder horizontally, wherein suitable aligning elements press from below against the diaphragm thus changing the position of the object holder. In this way a very accurate alignment of the object holder can be achieved without the need of touching the object holder. In particular, it is also possible to slightly lift the object holder from below with the aid of a suitable device and press the object holder against a second object holder plate.

The flexible material is particularly a diathermic diaphragm. Thereby, it is possible to provide heating elements, such as Peltier elements, below the individual receiving areas to heat individual object holders. By means of the receiving device according to the invention a very specific heating of possibly only individual partial regions of an object holder is possible without having to handle the object holder directly. In this case, damaging the object support is again avoided. Preferably, the diaphragm is designed such that temperatures of 4° C. to 100° C. can be transferred to the object holder.

To be able to use the receiving device according to the invention particularly in existing arrangements, the outer dimensions of the receiving device correspond to standard dimensions of microtiter plates. The receiving device has a width of 96±4 mm and a length of 128±4 mm in particular.

The method according to the invention is described below on the basis of the hybridization analysis of DNA fragments. The method is however in particular also suitable for other chemical and/or biological samples which have a verifiable affinity to each other, wherein the analyses may in particular be analyses of antigen-antibody affinities. For implementing the method described below, in particular the analyzing device described above is suitable.

In the method according to the invention, a first sample, e.g. DNA pieces, i.e. gene fragements, is arranged true-to-position at one or a plurality of locations at the base part, preferably a flat object holder. This may be effected by the first sample being dripped onto and subsequently adhering to fixed positions of the object holder.

In the next step, the base part is closed with a lid such that a test chamber is formed. The first sample is thus located inside the test chamber.

Subsequently, a second sample at least partly reacting on the first sample is supplied to the test chamber. This second sample may be the RNA of a tissue to be examined transformed into DNA with the aid of enzymes, as described in the introductory part. Said DNA of the second sample is preferably marked with a fluorescent marker.

In the next step according to the invention, the second sample located in the test chamber is moved by a conveying means, such as a pump. The movement is effected such that at least a portion of the sample is drawn off the test chamber and supplied back to the test chamber. As described above with regard to the analyzing device, this can be effected in different preferred ways.

When applying the method according to the invention, excellent analysis results can be obtained since the second sample is moved in the test chamber and thus DNA present in the second sample is capable of more easily detecting the DNA fragments in the first sample.

Movement of the sample is preferably performed by moving the second sample to and fro or circulating the second sample.

In a preferred embodiment of the method, a third sample is supplied, together with or after the second sample, to the test chamber. The third sample is a reference sample taken from healthy tissue. This DNA is preferably also marked with a suitable marker, in particular a fluorescent marker. With the aid of the conveying means both samples, i.e. the second and the third sample, are then jointly set into motion and/or kept moving inside the test chamber over longer periods of time of several hours.

When the reaction has taken place, i.e. possibly after more than 10 to 14 hours, the test chamber is preferably washed. By washing the test chamber the carrier substances of the samples and those portions of the samples which have not combined with a DNA piece fixedly adhering to the sample holder are washed off. Preferably, the base part and/or the object holder are dried after the washing. Preferably, a plurality of base parts located in the receiving device are jointly dried when the device comprising a receiving device for receiving a plurality of base parts, as described above, is used. Subsequently, i.e. after the washing and/or, drying of the base part, the base part and/or the base parts are fed to a detection means. In said detection means the sample is examined e.g. with the aid of a laser light source and corresponding detectors. When fluorescent color markers of different colors are used, the detected colors help to draw conclusions as to the type of tissue change and the like.

BRIEF DESCRIPTION OF THE DRAWINGS

Hereinafter, the invention will be explained in detail with respect to a preferred embodiment with reference to the accompanying drawings. In the Figures.

DETAILED DESCRIPTION OF THE PREFERRED EMBODIMENT

Figure 1:
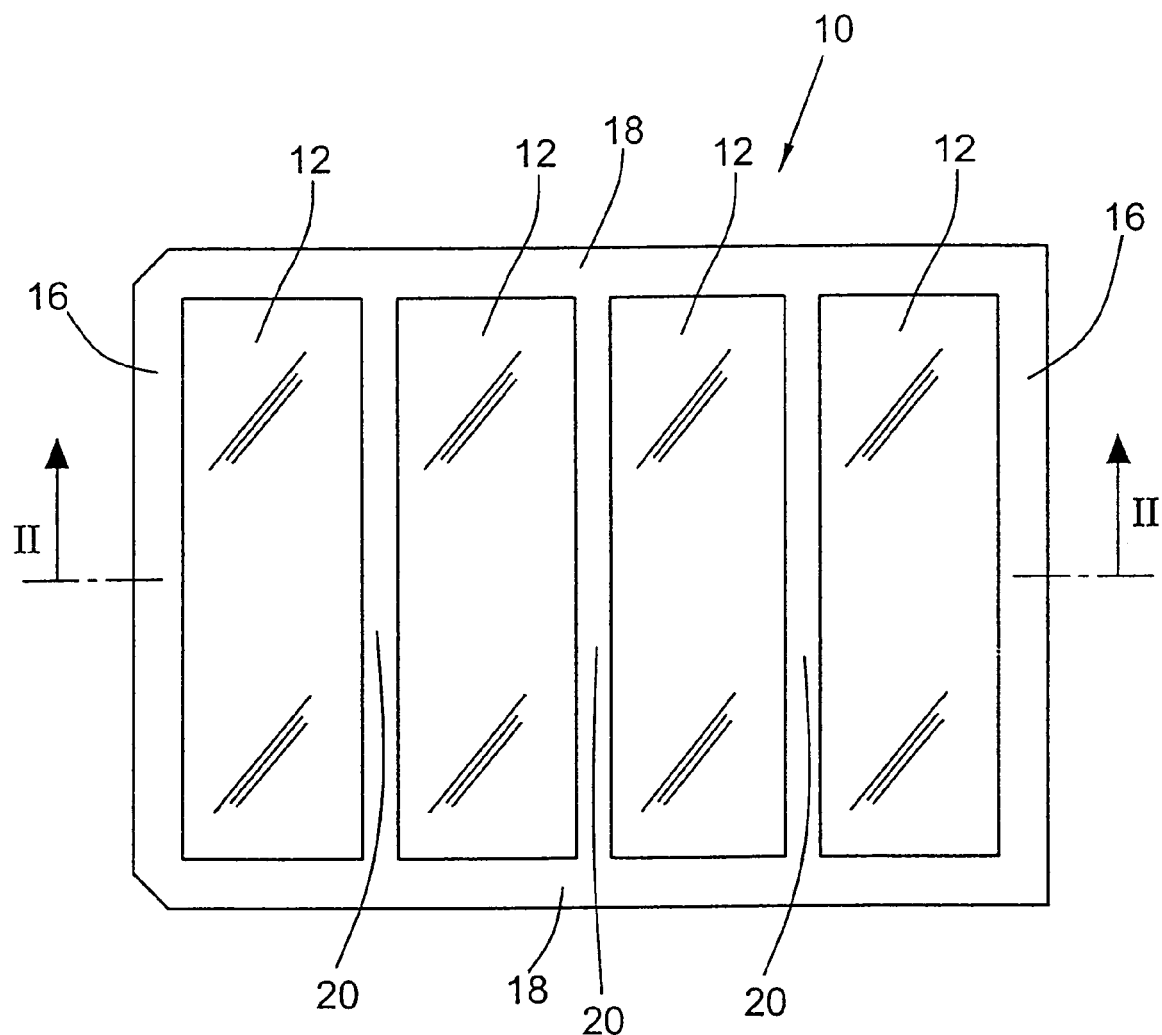
FIG. 1 is a schematic top view of a preferred embodiment of the receiving device with several inserted base parts.
Figure 2:
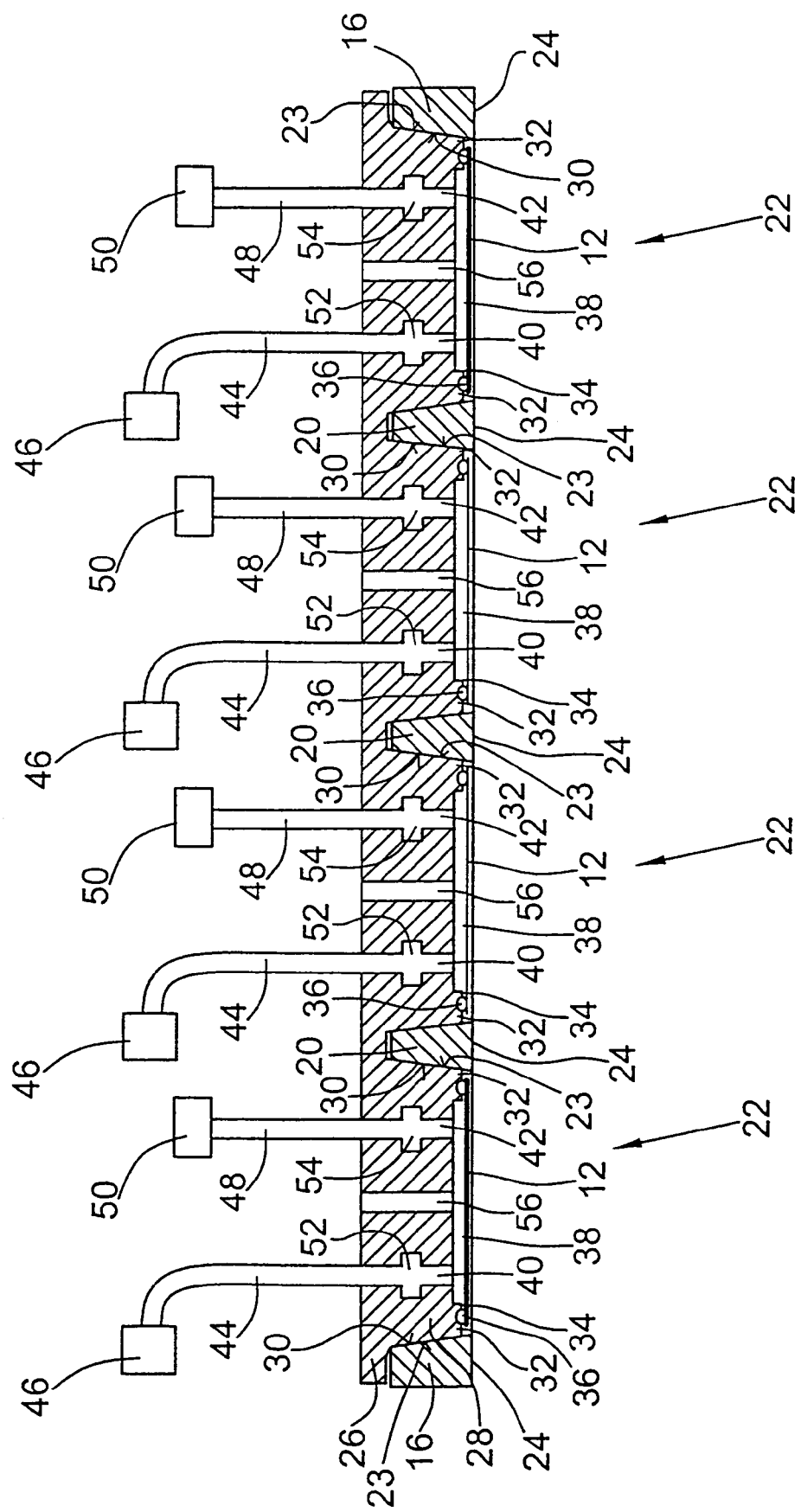
FIG. 2 is a schematic sectional view of a first preferred embodiment along the line II-II in FIG. 1, the head part not illustrated in FIG. 1 being additionally illustrated.

A receiving device 10 for several object holders 12 comprises a bottom part 14 (FIG. 2). The bottom part 14 is connected with centering elements 16,18, 20. In the illustrated embodiment, the centering elements 16,18,20 are arranged such that four rectangular receiving areas 22 are formed in each of which an object holder 12 can be arranged. The centering elements 16,18,20 have two opposing shorter side walls 16 and two also opposing longer side walls 18 arranged between the side walls 16. In the illustrated embodiment, three partition walls 20 arranged in parallel to the shorter side walls 18 are provided between the side walls 18.

At the undersides 24 of the centering elements 16,18,20, the bottom part 14 configured as a diaphragm is mounted. The receiving areas 22 hence have a flexible diaphragm as a bottom on which an object holder 12 is respectively supported. Thus, it is possible to press from below against the diaphragm in FIG. 2 in order to horizontally align the object holder, for example. Further, a heating element can be placed against the object holder 12 from below. Due to the flexibility of the diaphragm, the object holder 12 flatly lays against the surface of a flat heating element. Thereby, a uniform and good heat transmission between the heating element and the object holder is ensured.

At their insides 23, i.e. at the sides pointing toward the receiving areas 22, the centering elements 16,18,20 are chamfered. Thereby, the opening of the individual receiving areas pointing upwards in FIG. 2 is upwardly enlarged. This makes the insertion of the object holders 12 into the receiving areas 22 easier.

A lid or head part 26 is configured such that it projects into the individual receiving areas 22 formed between the centering elements 16,18,20. To this end, the lid 26 comprises four projections 28 in the illustrated embodiment which have a substantially rectangular cross-section. The side walls 30 of the projections 28 abut on the inner walls of the web-shaped centering elements 16,20. Likewise, side walls of the projection 28 not illustrated in FIG. 2 abut on the web-shaped centering elements 18. On the underside of the lid 26 facing the base part or sample holder 12, frame-shaped projections 32 are provided for each receiving area 22. The frame-shaped projection is configured as a circumferential projection. At an underside 34 of the frame-shaped projection 32, a seal 36 is provided which is also configured a circumferential seal. The seal 36 is supported on an outer border of the sample holder 12 and seals the sample holder with respect to the lid 26. Due to the frame-shaped projection 32, a test chamber 38 is formed between an inner side of the lid 36 and the sample holder 12 within the frame-shaped projection 32.

For moving samples provided in the test chamber 38, two channels 40,42 connected with the test chamber 38 are provided in the lid 26. The channel 40, for example, is connected to a pump 46 via a hose 44. Correspondingly, the channel 42 is connected with a pump 50 via a hose 48. The two pumps 46,50 are controlled by a preferably common control unit. The pumps 46,50 alternately suck a part of the sample located in the test chamber off into the channel 40 and 42, respectively, and subsequently deliver it into the test chamber 38 again. Thereby, a movement of the sample in the test chamber 38 is realized so that matching sample parts connect more easily if, for example, the device is used to analyze DNA affinities.

Further, two receiving chambers 52,54 are provided within the lid 26. The receiving chamber 52 is connected with the channel 40 and the receiving chamber 54 is connected with the channel 42. Due to the size of the receiving chambers 52,54, the sample quantity taken from the test chamber 38 can be collected. It is also possible that the two pumps 46,50 are directly connected with the receiving chambers 52,54 and are possibly arranged within the lid 26 or at the upper side thereof.

In order to supply a sample into the test chamber 38, a further channel 56 connected with the test chamber 38 is provided in the lid 26. After the lid 26 has already been set upon the receiving device 10, samples can be supplied through this channel 56 into the test chamber 38 which is already tightly sealed. Likewise, the sample can be supplied through one of the two channels 40,42, which is possibly branched for this purpose.

For improving the movement in the test chamber 38, the channels 40,42 may be branched so that several channels 40,42 are connected with the test chamber 38. Further, it is possible to provide a plurality of channels 40,42 per test chamber 38 in the lid 26. Preferably, half of the channels are connected with the same pump.

The lid 26 is held in a non-illustrated holding device. In FIG. 2, the holding device can be vertically moved. Because of the vertical movement of the holding device together with the lid 26, an automatic lowering of the lid 26 into the receiving areas 22 of the receiving device 10 is possible. In this case, the seal 36 provided at the frame-shaped projections 32 is pressed upon a border portion of the sample holders 12 and the test chamber 38 is formed. Since the sample holders 12 are supported on an elastic diaphragm serving as bottom part 14, damaging the sample holderss by lowering the lid 26 is avoided. Further, the elastic diaphragm 14 serves to ensure a tight sealing between the lid 26 and the sample holders 12.

Instead of moving the head part or lid 26, it is also possible to move the object holder 12 itself in upward direction in FIG. 2 to realize a tightly sealed test chamber 38. The object holder 12 can e.g. be pressed upwards with the aid of a stamp-shaped device which is capable of being vertically displaced. Further, a combination of these two movements is possible.

The test chamber 38 which, in the illustrated embodiment, essentially extends over the overall sample holder may be divided into a plurality of individual sample chambers. For this purpose, webs subdividing the test chamber 38 are arranged on the lower side of the lid 26. At the side of the webs pointing towards the sample holder 12 seals corresponding to the seals 36 for sealing the individual test chambers produced are provided. Each individual test chamber produced is, as described above, preferably provided with channels 40,52,56 and has the corresponding preferred configuration. Each individual test sub-chamber into which the test chamber 38 is subdivided can thus be filled with hybridization liquid independent of adjacent test chambers, and handled as described above. Due to the subdivision of the test chamber 38 into a plurality of test sub-chambers different samples can be examined in different ways using a standard object holder 12. In particular, identical samples taken e.g. from the bodies of different patients can be examined using the same hybridization liquids, or identical samples taken from the body of a patient can be examined using different hybridization liquids. In this connection it is particularly advantageous that commercial object holders can be used as sample holders 12.

Figure 3:
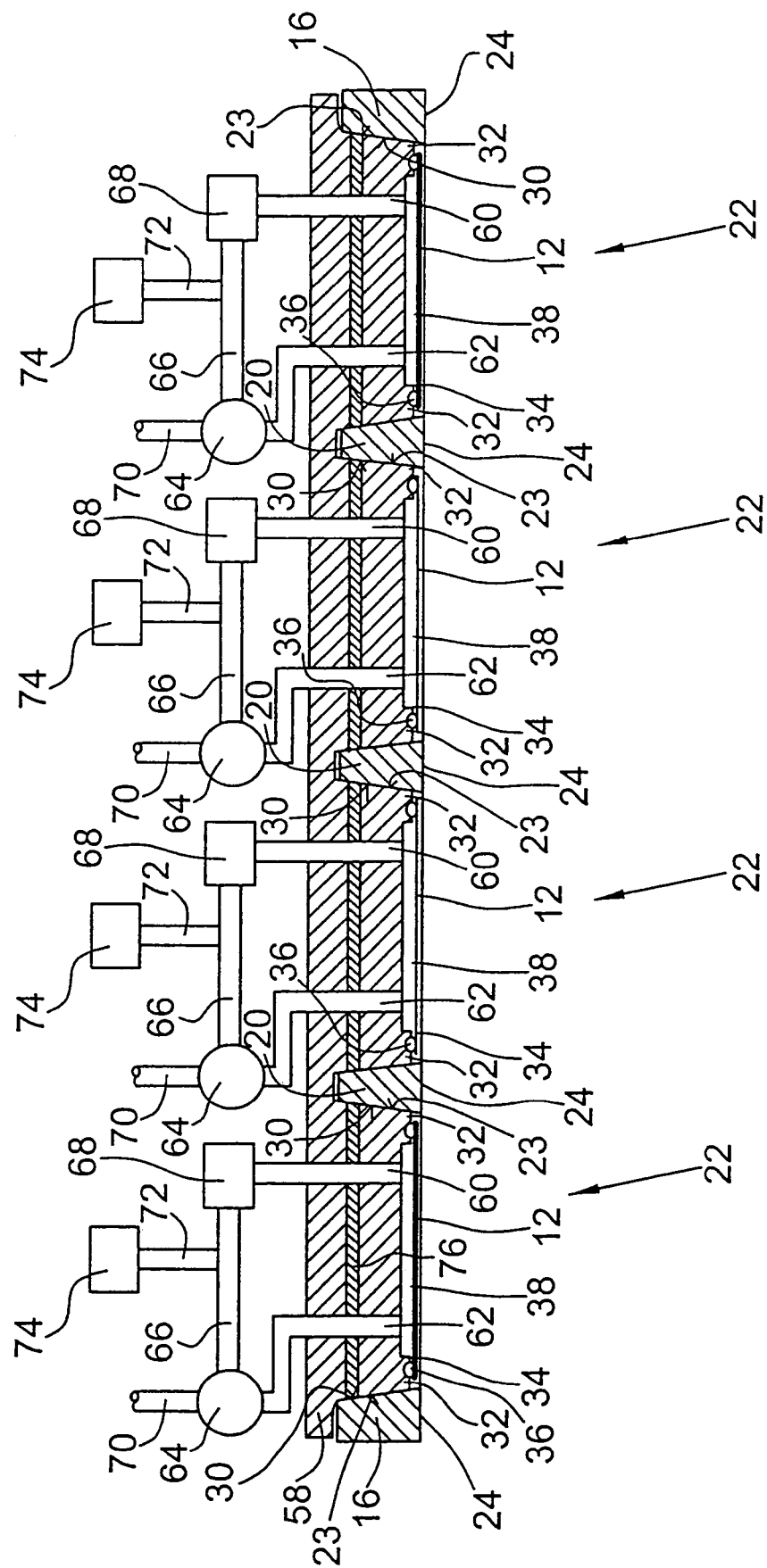
FIG. 3 is a schematic sectional view of a second preferred embodiment in principle corresponding to the embodiment shown in FIG. 2.

A second preferred embodiment (FIG. 3) comprises a lower area identical with that described with reference to FIG. 2. The lid or head part 58 is of different configuration in this embodiment. Identical or similar components of the device are designated with the same reference numerals in FIG. 3.

The head part 58 comprises a supply channel 60 connected with the test chamber 38 and a discharge channel 62 connected with the test chamber 38. The channel 62 is connected via a valve 64 and a channel 66 with a pump 68. The pump 68 is connected with the supply channel 66. The valve 64 is further connected with a drain 70. The channel 66 is connected via another channel 72 with a medium reservoir 74.

The position of the valve 64 can be e.g. selected such that the sample in the test chamber 38 is circulated. The sample is thus drawn off the chamber 38 via the discharge channel 62, supplied via the channel 66 to the pump 68 and then supplied via the channel 66 back to the test chamber 38.

To discharge a portion of the sample via the drain 70, the valve 64 can be arranged in an intermediate position such that a portion of the sample fed via the channel 62 to the valve 64 is supplied to the channel 70 and another portion to the channel 66.

Further, it is possible to set the valve 64 such that the channel 66 is closed and the entire sample is supplied towards the drain 70. For this purpose, the new sample liquid is supplied with the aid of the pump 68 from the reservoir 74 to the test chamber 38, and the sample contained therein is pressed out of the test chamber 38. To allow the entire sample to be exchanged, the channel 66 must also be emptied. For this purpose, the valve 64 is switched over after evacuation of the sample from the test chamber 38 such that the sample remaining in the channel 66 is pressed at least up to and into the channel 66. Subsequently, the valve 64 is opened again and the sample contained in the channel 66 of the test chamber 38 and the channel 62 is pressed into the drain 70.

Further, a heating element 76 is provided in the head part or lid 58, by means of which the temperature of the sample contained in the test chamber 38 can be regulated.

Preferably, a separate pump 68 is provided for each of the four test chambers 38 of the illustrated embodiment. Preferably, only one medium reservoir is provided for a plurality of, in particular for all test chambers 38. For a separate sample exchange in the individual test chambers 38 correspondingly controllable valves are provided in the channels.

Figure 4:
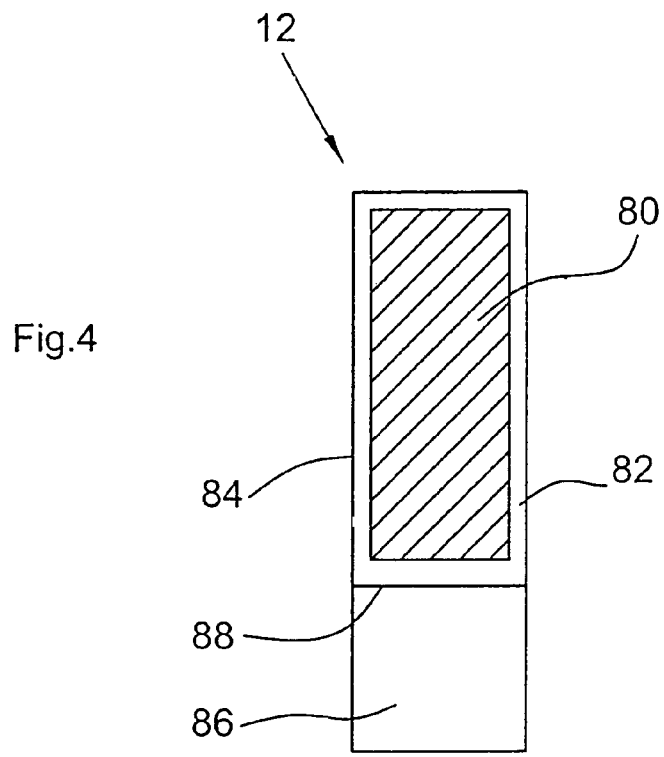
FIG. 4 shows a single base part being adapted to be inserted into the receiving device illustrated in FIG. 1.

The individual object holders 12 serve, for example, for analyzing DNA samples. To this end, each object holder, as illustrated in FIG. 4, is divided into different areas. In an inner area 80, sample droplets are applied, for example, which then firmly connect to the sample holder 12. Thus, the area 80 serves as a surface for arranging an array. The area 80 is surrounded by a preferably 2.5 mm wide margin 82. The margin 82, for example, is provided for the purpose that all the samples in the area 80 have a sufficient distance to the outer edges 84 of the object holder 12. With the lid 26 being lowered, the seal 36 is supported in the margin area 82. An area 86 separated from the margin 82 by the line 88 shown in FIG. 4 serves for touching the sample holder 12. In this area no samples are disposed so that the object holder 12 can be handled in the area 86. The touch area 86 is required, for example, to allow the object holder 12 to be inserted into the receiving device 10 according to the invention.

Figure 5:
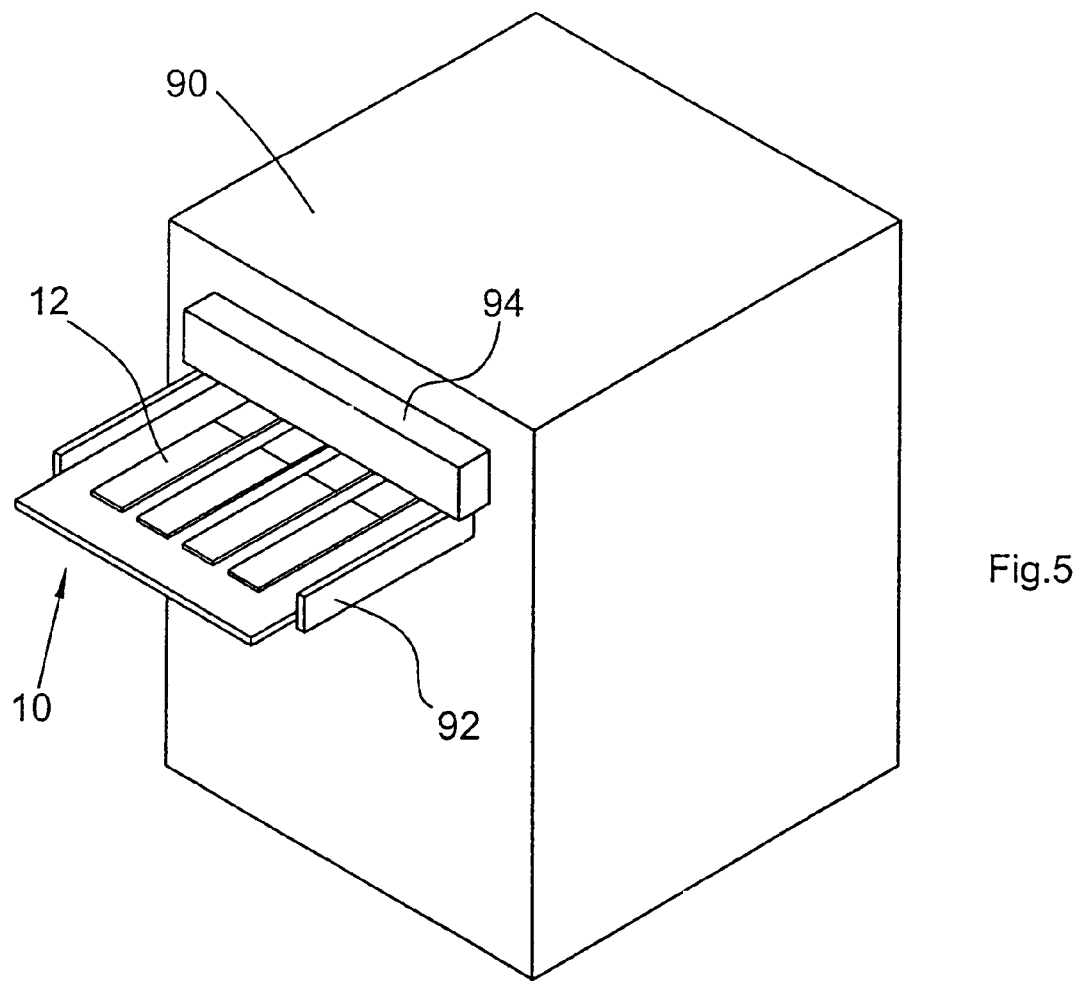
FIG. 5 is a schematic perspective view of an analyzing device into which the receiving device is adapted to be inserted.

The receiving device 10 can be inserted into an analyzing device 90 (FIG. 5) comprising a hybridization head and the lid 26, respectively. To this end, the analyzing device 90 comprises a drawer-like receiving means 92 for receiving the receiving device 10. The drawer may be configured in correspondence with a drawer of a CD player or the like. When the drawer 92 is open, the receiving device 10 supporting the object holders 12 is inserted into the drawer from above and then displaced into the analyzing device 90.

Within the analyzing device 90, the lid 26 is arranged such that it is lowered downward upon the object holders 12 after the receiving device 10 has been displaced into the analyzing device 90.

Additionally, a drying head 94 is provided above the drawer 92. The drying head 94 is provided with a fan. After the hybridization process has been completed, the drawer is displaced out of the analyzing device 90 again. In doing so, the sample or washing liquid remaining on the object holders 12 is removed by means of the drying head 94. Preferably, the drying head has several outlet and inlet openings. By the inlet openings, the air delivered by the drying head or another drying medium is sucked in again. Thereby, it is avoided that sample liquid components reach the surroundings. In this connection, the cross-sectional area of the suction inlet is larger than that of the outlet so that the drying head 94 always sucks in more air than it delivers. Thereby, the danger of components of the sample reaching the surroundings is further reduced. The inlets and/or outlets may be slot-shaped openings extending over the width of the drying head.

To ensure a complete drying of the sample holders 12, the drawer 92 may be displaced back and forth several times.

Additionally, it is possible to wash the sample holders before drying them. Preferably, this is done by means of the lid 26, i.e., when the test chambers 38 are still sealed. Thus, the washing procedure is performed within the analyzing device. To this end, a washing liquid can be supplied via separate channels provided in the lid 26 or via the channels 40,42 of the test chamber and drained therefrom again. Before the lid is displaced upwards within the analyzing device and the test chamber 38 is no longer tight therefore, the liquid in the test chamber is preferably sucked off to a large extent. Sucking off, in turn, is preferably effected via the channels 40,42 already present.

The invention claimed is:

1. Analyzing device for analyzing chemical and/or biological samples, comprising
    a test chamber for receiving the sample, formed by a base part and a head part, and
    a moving means for moving the sample in the test chamber,
    wherein the moving means comprises a conveying means for drawing off the test chamber at least a portion of the sample and supplying said portion of the sample back to the test chamber.

2. Analyzing device according to claim 1, wherein the conveying means is connected with a receiving chamber for receiving and subsequently delivering a portion of the sample.

3. Analyzing device according to claim 2, wherein at least two receiving chambers are provided which alternately receive and deliver a portion of the sample.

4. Analyzing device according to claim 2, wherein at least one receiving chamber is provided in the head part.

5. Analyzing device according to claim 1, wherein the head part comprises a supply channel for supplying the sample to the test chamber.

6. Analyzing device according to claim 1, wherein the conveying means is connected via a supply channel and a discharge channel with the test chamber for circulating the sample.

7. Analyzing device according to claim 1, further comprising a valve arranged in the discharge channel, said valve being connected with a drain.

8. Analyzing device according to claim 1, further comprising a medium reservoir connected with the conveying means.

9. Analyzing device according to claim 1, wherein the test chamber is formed by a circumferential frame-shaped projection provided at the head part.

10. Analyzing device according to claim 9, wherein the projection comprises a seal.

11. Analyzing device according to claim 1, wherein the base part is a flat object holder.

12. Analyzing device according to claim 1, further comprising a receiving device for a plurality of object holders, comprising
    a bottom part, and
    centering elements connected with the bottom part, wherein the centering elements are arranged such that a plurality of receiving areas for receiving one object holder each are formed.

13. Analyzing device according to claim 12, wherein the centering elements are formed by integral frame parts and the frame part is configured such that each receiving area is surrounded by a circumferential centering frame.

14. Analyzing device according to claim 12, wherein the centering elements are chamfered in the direction of the receiving area.

15. Analyzing device according to claim 12, wherein the bottom part is made of a flexible material, at least in the receiving areas.

16. Analyzing device according to claim 15, wherein the flexible material is a diathermic flexible diaphragm.

* * * * *